United States Patent
Suzuki et al.

(10) Patent No.: US 8,859,010 B2
(45) Date of Patent: Oct. 14, 2014

(54) METHOD OF PRODUCING EGGSHELL POWDER

(75) Inventors: Fred K. Suzuki, Arlington Heights, IL (US); Pie-Yi Wang, Wheaton, IL (US); J. B. Weatherspoon, Glen Ellyn, IL (US); Laurence C. Mead, Hoffman Estates, IL (US)

(73) Assignee: Biosynergy, Inc., Elk Grove Village, IL (US)

( * ) Notice: Subject to any disclaimer, the term of this patent is extended or adjusted under 35 U.S.C. 154(b) by 0 days.

(21) Appl. No.: 10/535,779

(22) PCT Filed: May 28, 2004

(86) PCT No.: PCT/US2004/016913
§ 371 (c)(1),
(2), (4) Date: Aug. 4, 2005

(87) PCT Pub. No.: WO2004/105912
PCT Pub. Date: Dec. 9, 2004

(65) Prior Publication Data
US 2006/0062857 A1  Mar. 23, 2006

Related U.S. Application Data

(60) Provisional application No. 60/474,175, filed on May 29, 2003, provisional application No. 60/575,336, filed on May 27, 2004.

(51) Int. Cl.
| | | |
|---|---|---|
| *A61K 33/32* | (2006.01) | |
| *A61K 9/14* | (2006.01) | |
| *B09B 3/00* | (2006.01) | |
| *A23K 1/175* | (2006.01) | |
| *A61K 33/08* | (2006.01) | |
| *A23L 3/3472* | (2006.01) | |
| *A61K 35/56* | (2006.01) | |
| *A61K 33/30* | (2006.01) | |
| *A23L 3/358* | (2006.01) | |

(52) U.S. Cl.
CPC . *A61K 33/08* (2013.01); *B09B 3/00* (2013.01); *A23K 1/1758* (2013.01); *A23L 3/3472* (2013.01); *A23K 1/1753* (2013.01); *A61K 35/57* (2013.01); *A61K 33/30* (2013.01); *A23L 3/358* (2013.01)
USPC ............................................ 424/641; 424/489

(58) Field of Classification Search
USPC .................... 424/601, 489, 641; 514/492
See application file for complete search history.

(56) References Cited

U.S. PATENT DOCUMENTS

| | | |
|---|---|---|
| 2,376,672 A | 5/1945 | Dreyling |
| 2,419,822 A | 4/1947 | Contesso |

(Continued)

FOREIGN PATENT DOCUMENTS

| | | |
|---|---|---|
| JP | 01-01765 | 4/1989 |
| JP | 07-017711 | * 1/1995 |

OTHER PUBLICATIONS

Unitied States Department of Labor Occupational Safety & Health Adminstration, Occupational Safety and Health Guideline for Zinc Oxide, printed from http://www.osha.gov/SLTC/healthguidelines/zincoxide/recognition.html on Jul. 1, 2010, 12 pages.*

(Continued)

*Primary Examiner* — Gigi Huang
(74) *Attorney, Agent, or Firm* — Michael Best & Friedrich LLP

(57) ABSTRACT

The invention relates to producing dried eggshell powder in conditions of high temperatures, preferably in first, second and third heating stages to isolate specific components of the eggshell. These components have nutritional and anti-microbial activity.

7 Claims, 2 Drawing Sheets

(56) References Cited

U.S. PATENT DOCUMENTS

| | | | |
|---|---|---|---|
| 5,045,323 A * | 9/1991 | Michalek | 424/601 |
| 5,409,714 A * | 4/1995 | Ishijima | 424/693 |
| 5,811,147 A | 9/1998 | Yamada | |
| 6,176,376 B1 | 1/2001 | MacNeil | |
| 6,365,193 B1 | 4/2002 | Sasaki et al. | |
| 6,627,229 B2 | 9/2003 | Kikuchi et al. | |
| 2001/0043953 A1* | 11/2001 | Kikuchi et al. | 424/687 |
| 2005/0159324 A1 | 7/2005 | Man et al. | |
| 2006/0062857 A1 | 3/2006 | Suzuki et al. | |

OTHER PUBLICATIONS

PCT/US04/16913 International Search Report dated Dec. 15, 2004 (1 pages).

Russell et al. "Monochloramine Versus Sodium Hypochlorite as Antimcrobial Agents for Reducing Populations of Bacteria on Broiler Chicken Carcasses" in Journal of Food Protection, vol. 68, No. 4, 2005, p. 758-763.

United States Patent Office Final Rejection for U.S. Appl. No. 11/108,584 dated May 2, 2012 (10 pages).

United States Patent Office Action for U.S. Appl. No. 11/108,584 dated Aug. 29, 2011 (2 pages).

United States Patent Office Action for U.S. Appl. No. 11/108,584 dated Jun. 10, 2010 (11 pages).

United States Patent Office Final Rejection for U.S. Appl. No. 11/108,584 dated Oct. 14, 2009 (17 pages).

United States Patent Office Action for U.S. Appl. No. 11/108,584 dated Dec. 17, 2008 (17 pages).

United States Patent Office Action for U.S. Appl. No. 11/108,584 dated May 21, 2008 (12 pages).

United States Patent Office Action for U.S. Appl. No. 13/667,571 dated Feb. 7, 2013 (10 pages).

* cited by examiner

METHOD OF PRODUCING EGGSHELL POWDER

CROSS-REFERENCE TO RELATED APPLICATIONS

This is a U.S. national stage entry of International Patent Application No. PCT/US2004/016913, filed on May 28, 2004, which claims priority to U.S. Patent Application No. 60/575,336, filed on May 27, 2004, and U.S. Patent Application No. 60/474,175, filed on May 29, 2003, the entire contents of all of which are fully incorporated herein by reference.

FIELD OF THE INVENTION

This invention relates to a method of producing a dry, eggshell powder of specific particle size which is free of pathogens. More particularly, the invention relates to a method of producing dry eggshell powder under conditions of high temperatures. Further, the invention relates to a method of producing a dry eggshell powder with first, second and third heating stages to isolate favored components of the eggshell.

BACKGROUND OF THE INVENTION

There is a need for the food processing industry to find alternative methods for processing and using eggshells in a way that is beneficial to the environment. In the United States, there are about 190,000 tons of wasted eggshells generated by egg processing and hatchery plants annually. From this amount, about 120,000 tons are generated from egg processing plants and about 70,000 tons are generated from hatcheries. When eggshells are stored at room temperature, they are rapidly degraded causing unpleasant sulphurous odors. Typically, eggshells are disposed in a landfill, currently the most common and economical disposal method. Landfill deposition costs range about $20-40 per ton, where it is permitted. In many states, landfill disposal of eggshells is not permitted. The landfill disposal produces methane, carbon dioxide and other volatile organic chemicals.

Eggshell contains about 4% organic matter and a substantial amount of calcium and other minerals, including magnesium and zinc. Dried eggshell particles contain approximately 94% calcium carbonate, with 39% of the compound being absorbable calcium. Natural calcium sources not only contain calcium but also magnesium, phosphorous and zinc.

U.S. Pat. No. 5,045,323 describes a method for preparing compounds from eggshells, particularly from the chicken eggshell, which could be utilized for medical purposes for treating certain diseases and for replacement of deficient materials in living tissues. The method includes drying eggshells using hot air at a temperature of up to 150° C. The dried eggshells are then ground to a particle size of 10-80 microns. After drying, the temperature is lowered to 50° C. The dried eggshell powder only contains carbonate compounds and does not possess anti-microbial properties.

U.S. Pat. No. 6,176,376 describes a method and apparatus for separating the membrane layers from the inside of eggshells by mixing with water. The eggshell particles and membrane particles are separated for further processing. The eggshell membrane contains about 10% collagen that is used for skin grafts, dental implants, cornea repair and other medical uses. The purified eggshells are also used in paper or agriculture industries as lime substitutes or calcium supplements.

U.S. Pat. No. 5,409,714 describes an anti-microbial agent containing a calcined calcium oxide prepared by calcining oyster shells and/or a calcined product of a calcium hydroxide or hydrated product of calcium hydroxide. The particle size of the product is less than or equal to 74 microns. It can be applied to processed food in a liquid state ranging in amounts from 0.05% to 10% by weight. The product comprises a combination of a calcined calcium oxide type and the calcined product of calcium hydroxide. The ratio of the types of calcium oxide ranges from 3 to 7 parts to approximately 7 to 3 parts. The examples in the disclosure show uses of the product as a preservative of various food articles, namely rice, ice cream, cucumbers, eggs, cuttlefish and edible jellyfish. Since the oyster shells come from the ocean, the mineral content of the shells is not precisely controlled as it is in eggshells because of the specialized formulation of poultry feed. The oyster shell may have a less consistent chemical composition than eggshells and have more heavy metal contamination.

U.S. Pat. No. 2,419,822 describes a process for production of calcium carbonate from eggshells. Eggshells are placed in a drum having rotating internal blades which crush the shells in the presence of hot water. Rotation of the blades is stopped and the drum is drained of water and impurities, and subsequently the drum is closed and the blades are rotated again with the emission of hot air to dry the eggshells. The crushed shells are then removed and ground under oxygen to produce a dry bacteria-free product.

While the foregoing methods of utilizing eggshells and hatchery waste, none can remedy the problem of large-scale disposal of eggshells. The present invention provides an improvement in the art by treating eggshell to provide a dry pathogen-free eggshell powder that has many applications.

SUMMARY OF THE INVENTION

The present invention describes a method of producing a dry eggshell powder having a specific particle size and being free of pathogens. The calcining temperature ranges from about 350° C. to about 600° C. to about 1200° C. The process may be interrupted at various stages to yield eggshell powders comprising substantial amounts of zinc oxide, magnesium oxide and calcium oxide, respectively.

It is an object of the present invention to produce a dry eggshell powder.

Another object of the present invention is to provide an alternative to disposing of eggshells in landfills.

Another object of the present invention is to calcine eggshells at temperatures greater than 850° C.

Another object of the present invention is to produce eggshells with first, second and third heating stages to isolate components in the eggshell.

It is another object of the present invention to produce an eggshell powder that is free of pathogens and has various applications.

Other objects, features and advantages of the present invention can be derived from the description. The foregoing features and those which are further described below can be likewise utilized in accordance with the invention.

DESCRIPTION OF THE INVENTION

Figure 1:
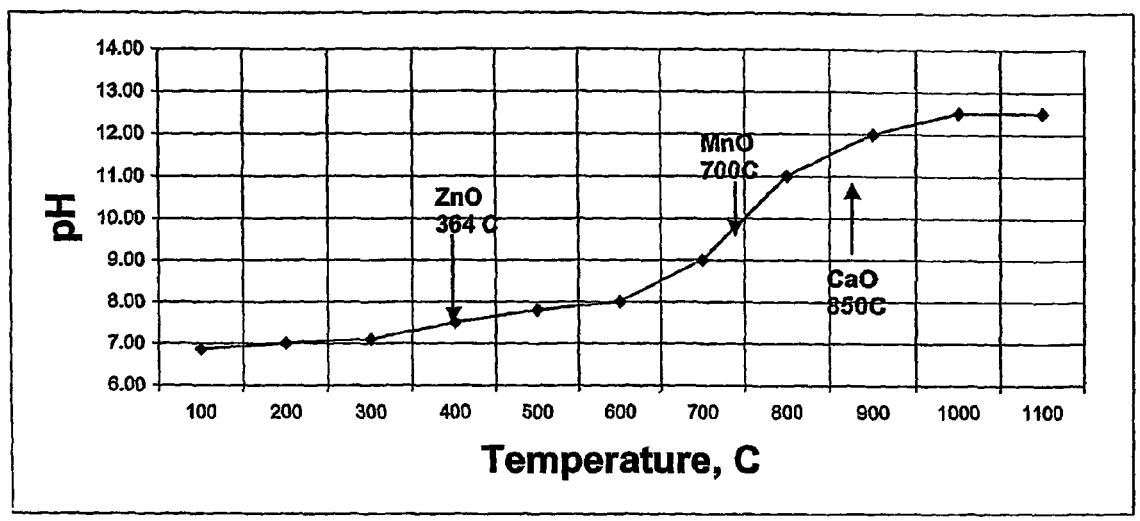
FIG. 1 is a graphical representation of calcining temperatures and pH levels for certain metals found in a raw eggshell.

The present invention provides a method of calcining eggshells, preferably shells from chicken eggs, at various temperature ranges, to produce an eggshell powder. The eggshell powder can be utilized as a food additive, anti-microbial agent, fertilizer, etc. The present invention also serves to obviate eggshell disposal problems for egg producers and to alleviate environmental concerns. In addition, the method may utilize specific heating and timing conditions for the raw eggshells to produce eggshell powder with substantial amounts of specific metal oxides. Calcining temperatures in the present invention may vary so that the eggshell powder may contain significant amounts of zinc oxide, magnesium oxide and calcium oxide, respectively.

Calcination is the heating of a solid below the melting point to create a state of thermal decomposition or phase transition other than melting. Reactions that may occur while heating a solid to below its melting point include a) thermal dissociation, and b) thermal recrystallization.

The foregoing reactions are evident in the calcining of eggshells. The organic matter in the eggshells, the membrane and egg whites, etc., are heated and distilled to yield concentrated reaction products from protein such as urea and ammonia. Other highly concentrated by-products may include silver, iodine in the free state or as salts. The eggshell itself undergoes a phase transition from a solid to an amorphous state before being cooled, dried and pulverized to a powder.

The calcined eggshell contains ingredients, for example, metals or heavy metals which may increase the functional value of the calcined eggshell powder. An analysis of the ingredients in calcined eggshell is found in Table 1.

TABLE 1

Egg Shell

| Assay | Analysis | Units |
|---|---|---|
| PH | 12.1 | |
| Arsenic | <3.0 | PPM |
| Antimony | <.10 | PPM |
| Heavy Metals | <20 | PPM |
| Lead by Graphite Furnace | 171 | PPB |
| Mercury | .025 | PPM |
| Selenium | .066 | PPM |
| Silver | 8.29 | PPM |
| Sulfur | .034 | % |
| Tin | <500 | PPM |
| Aluminum | <20 | PPM |
| Barium | 30.9 | PPM |
| Beryllium | <5 | PPM |
| Cadmium | <5 | PPM |
| Calcium | 655000 | PPM |
| Chromium | <10 | PPM |
| Cobalt | <5 | PPM |
| Copper | <2.5 | PPM |
| Iron | 10 | PPM |
| Magnesium | 5440 | PPM |

TABLE 1-continued

Egg Shell

| Assay | Analysis | Units |
|---|---|---|
| Manganese | <1.5 | PPM |
| Nickel | <4 | PPM |
| Phosphorous | 1470 | PPM |
| Potassium | <500 | PPM |
| Sodium | 610 | PPM |
| Strontium | 352 | PPM |
| Vanadium | <5 | PPM |
| Zinc | 3.04 | PPM |

Useful products are obtained in the method of the present invention that involves a heating system that alternatively can be divided into three zones, stages or heating periods. In a first heating period, a calcining temperature of about 350° C. may be utilized to calcine zinc oxide in the eggshell. Zinc carbonate is converted to ZnO, which has beneficial effects as an antibacterial agent. The pH of zinc oxide formed at about 350° to 400° C. is about 8.25. At this temperature magnesium and calcium are carbonate salts. Alternatively, the calcined zinc oxide may be subjected to continued heating in the system at higher temperatures where other metal oxides are formed. The eggshell particle with concentrated zinc oxide contained therein may have valuable uses. At this temperature, protein from the organic matter in the eggshell is intact and may be useful in a nutritional feed product for cattle, swine, and chickens, etc., or as a preservative.

A higher calcining temperature may be utilized in a second heating zone or period wherein magnesium oxide may be produced at a temperature of about 600° C. from magnesium carbonate. At 500° C. the eggshell may contain about 75% magnesium carbonate and 25% magnesium oxide, whereas at 600° C. there is a full conversion to magnesium oxide from the carbonate. The pH of the magnesium oxide is about 10-11 which provides bacteriostatic qualities to the magnesium oxide. Further, with oxygen escaping from the magnesium carbonate molecules during heating, the pore size of the compound increases thereby rendering improved water solubility to the compound. The resulting eggshell powder, rich in magnesium oxide, may be utilized as a food or feed additive and as an antibacterial agent.

The conventional calcining temperature for calcium is 900° C. The present invention is also directed to heating eggshells above that temperature but below the melting point to create eggshell powder that has anti-microbial activity, due mainly to its pH level. Anti-microbial activity is seen in eggshell calcined at temperatures ranging from 1000° C. to 1200° C. The pH of the calcium oxide is 11.5 at 850° C. The complete conversion of calcium carbonate to calcium oxide occurs at about 1200° C. with a pH of about 12.4. The heating, similar to magnesium carbonate, causes oxygen to escape thereby increasing the porosity and surface area of the compound to render it more bioavailable for food use. This information is described in FIG. 1 and Table 2. The heating may take place in the method in a third heating zone or period.

TABLE 2

| | 100° C. | 400° C. | 500° C. | 650° C. | 700° C. | 850° C. | 900° C. | 1000° C. | 1200° C. |
|---|---|---|---|---|---|---|---|---|---|
| $CaCO_4$ | | pH6.5 | pH 7.78 | pH 8.0 | | pH 11.5 50% $CaCO_4$ 50% CaO | | | 100% CaO with increased porosity, more surface area |

TABLE 2-continued

| | 100° C. | 400° C. | 500° C. | 650° C. | 700° C. | 850° C. | 900° C. | 1000° C. | 1200° C. |
|---|---|---|---|---|---|---|---|---|---|
| $MgCO_4$ | pH 6.9 | | 75% $CO_4$ 25% MgO | 1007. pH 10–11 | bacteriostatic properties, increased pore size, increased solubility | | | | |
| $ZnCO_4$ | | 364° C. ZnO 100% bacteriostatic agent pH 8.25 | | | | | | | |

The Table describes the loss of carbonate salt of the selected metals, all found in eggshells to yield the metal oxide with valuable functionality. The increasing pH of the oxide salts correlates with the conversion of carbonate to the oxide. The increased pH provides antibacterial and/or bacteriostatic properties to the oxide salts. Increased porosity is also a result of the calcining; typically improving the water solubility of the metal salts as the calcining temperatures increase for calcine carbonate, magnesium carbonate and zinc carbonate.

FIG. 1 is a graphical representation of the temperatures and pH correlation of metal oxide as they are found in the method of the present invention.

The temperature markers indicate a significant change in the conversion of the carbonate salt to the oxide of the metals. At 364° C., it was found that ZnO was completely formed from the starting material. At 650° C.-700° C., MgO was completely converted by heat to the oxide salt. Concerning calcium, the carbonate and oxide salts equally are present at about 850° C., with complete conversion to the oxide at 1200° C.

In the process, oxide salts of metals, specifically zinc, magnesium and calcium found in eggshells can be formed and separated in the calcining process independent of the remainder of the eggshells being heated. Each batch, taken from its respective heating zone or stage in the process is then cooled, dried and reduced in size to form a powder. The particle size of the eggshell is reduced to about 150 microns.

Alternatively, CaO can be specifically formed in the process by having the eggshell pass through all the zones wherein the preferred temperature is used, 1200° C., for converting 100% CaCO. Other metal oxides can be individually produced.

A preferred feature of the present invention is to operate the process wherein three different metal oxides are produced in a continuous process. Oxides of other metals found in eggshells can be produced in this process, however, zinc, magnesium and calcium oxides are preferred.

Figure 2:
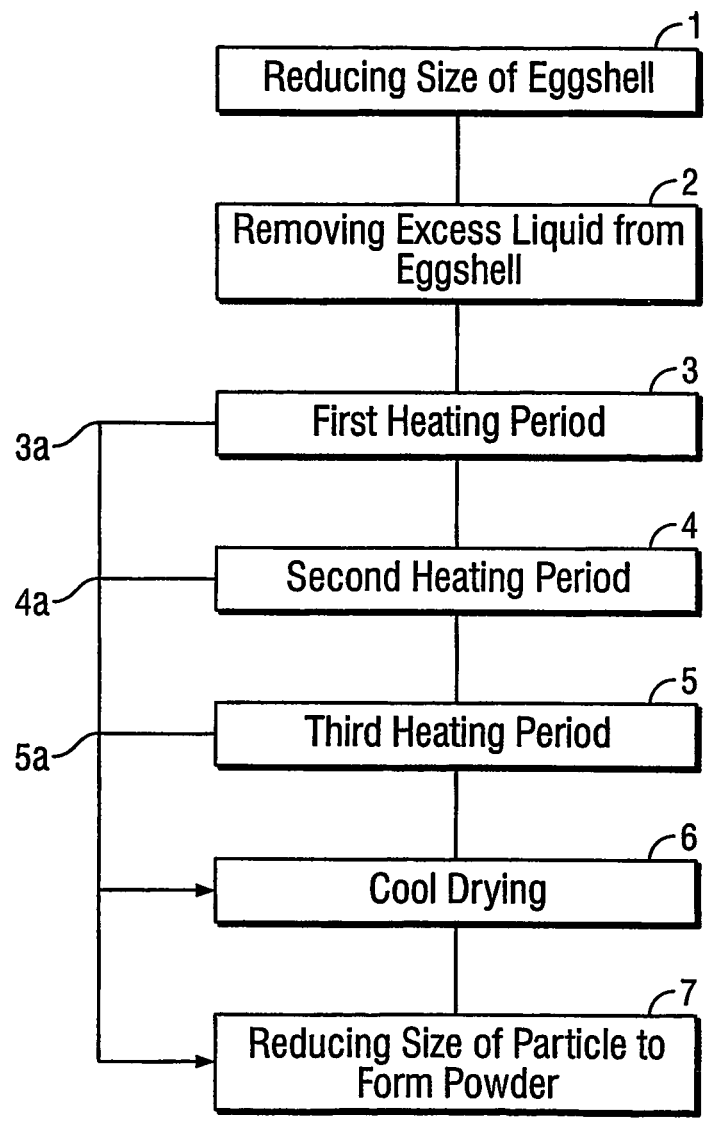
FIG. 2 is a description of a schematic flow diagram showing the method of the present invention.

With reference to FIG. 2, after eggshells are broken and the egg white and yolk are removed, the shells are reduced in size by crushing as shown in step 1. The preferred size of the eggshell particles is about ¼ inch diameter. After sizing, liquid is removed from the eggshell as shown in step 2 by conventional means, for example, by centrifugation. The eggshell particles are then placed in a heating apparatus for calcination. The heating apparatus may have means for moving the eggshell particles through its length, for example, a screw or conveyor. The heating apparatus may be divided into independently controlled heating zones to allow for thorough calcination of the eggshell particles. A cooling zone can also be included wherein purge air can be introduced into the heating apparatus to cool the calcined eggshell.

In step 3, heating of the eggshell particles commences. The temperature of the heating step is dependent on the desired calcined component of the eggshell. Zinc oxide may be calcined in the eggshell particles at temperatures ranging from 350-500° C. For magnesium oxide, the calcining temperature may range from 500-700° C. The heating may take place in step 4. When desiring the major component of the eggshell to yield calcium oxide, the calcining temperature must be over 800° C., preferably 1000-1200° C. This heating takes place in the third heating period or zone, step 5. At lower temperatures, about 600-700° C., calcium carbonate is the predominate component of the eggshell particles. Depending on the desired component in the eggshell to be isolated, heating may take place in steps 3, 4 and 5 or in one heated zone, allowing the eggshell particle to pass through. In each step 3, 4 and 5, after the calcined eggshell passes through the heating apparatus the eggshell is cooled and dried at step 6 by conventional means such as a water jacket containing cool water, to a temperature of about 35° C. to about 45° C.

The calcined eggshell particles are then reduced in size to form a powder by the use of a conventional milling machine or similar apparatus in step 7. A suitable milling system is Micro ACM manufactured by Hosokawa Micron, GmbH. The particles are milled to a size of about 50 microns.

Alternatively, the heated eggshells may exit each heating zone or period at 3a, 4a and 5a to be cooled, dried and milled to form a powder.

The resident time for heating the eggshell particle is dependent on the metal oxide to be formed. The eggshells are heated for an effective amount of time to yield the oxide salt of the metal.

EXAMPLE 1

Crushed eggshells were obtained from a laying operation. The shells were centrifuged to remove organic matter and moisture. The eggshells have a moisture level of 11.5%. The shells were fed into a rotary calciner made by Alstom Power of Naperville, Ill. The cylinder comprises three sections: a feeding section, a calcining section and a cooling section. The feeding and cooling sections are made from stainless steel. The calcining section is housed in a furnace constructed with high temperature alloy and approved by the Food and Drug Administration and the United States Department of Agriculture to provide a maximum operating temperature of 1200° C. The feeding and calcining sections are insulated and the cooling section is a bare, stainless steel tube to provide a cooling effect. The calcining section contains three heating zones, with each zone temperature being controlled independently. The feeder is set to deliver at a rate of 50 pounds per minute.

The cylinder rotation speed is adjusted to obtain 50 minutes calcining time in the heating zones. The temperature of zones 3, 4 and 5 are set at 900, 1000 and 1100° C. The crushed eggshells are fed into the device and at heating zone 3 they show a black color and at the end of zone 5, when all zones are used, the product is a white color, which indicates that the organic matter has been permanently decomposed and evaporated. The crushed eggshell or eggshell flakes enter the device at about 25° C. and between zones 3 and 4 reach a temperature of about 900° C. At the end of zone 5, the product is at a temperature of 1060° C. After cooling, the product temperature is reduced to 50° C. The cooled product is then milled to 1 to 50 micron particle size. The eggshell powder has the composition shown in Table 1. The pH of a 0.125% eggshell powder solution in water is about 12.2.

The anti-microbial properties of eggshell powder are illustrated in Example 2. With the various concentrations of the calcined eggshell powder in the growth medium, growth of *Pseudomonas, Listeria monocytogenes, E. coli* yeast and lactic acid bacteria was inhibited, and in many of the test samples, the calcined eggshell powder product produced better results than the oyster shell powder.

EXAMPLE 2

The objective of this study was to assess the efficacy of two preservative systems in inhibition of the growth of pathogenic and spoilage organisms in laboratory media.

Background

Two products ESP-1 (Egg Shell Powder) and OP-1 (Oyster Shell Powder) established in Japan are presented as preservatives for food and beverage products.

A challenged study was conducted in which the products were added at at concentration of 1%, 0.5%, 0.25%, 0.125% and 0.05% (w/w) into laboratory growth media and these solutions inoculated with typical spoilage and pathogenic organisms including *Listeria monocytogenes*, mold, yeast, lactic acid bacteria, *Pseudomonas, Escherichia coli* (0151-H7).

Materials and Methods

Test Product

Two class screw cap vials with 15 g each of test preservative are prepared in the method of Example 1 of the U.S. Pat. No. 5,409,714 was followed to prepare oyster shell powder, a known antimicrobial agent, and is identified as of OP-1. ESP-1 the product of the process of the present invention, was prepared in accordance with the procedures described in Example 1. Samples were stored at room temperature prior to the initiation of the study.

Challenge Organisms

Samples were inoculated with the following composite cultures prepared from strains obtained from bioMerieux, Hazelwood, Mo.: A cell suspension was prepared for each strain, cell suspension were mixed to prepare an inoculum which contained approximately equal number of cells or each strain, the number of viable cells or spores was verified by optical density confirmed by conventional plate count method.

| Organism | bioMerieux ATCC# |
|---|---|
| *Pseudomonas aeruginosa* | 21853 |
| *Listeria monocytogenes* | 1644 |
| *Candida albicans* (yeast) | 10231 |
| *Lactobacullus brevis* (lactic acid bacteria) | 4366 |
| *Escheria coli* (0151-H7) | 100128 |

Preparation of Test Samples and Storage

For each challenge organism, 1.0, 0.5, 0.25, 0.125, 0.05% (w/w) of test preservative was added to growth medium* as listed below. The solutions were mixed thoroughly. A composite culture was added at 10-100 cfu/ml (colony forming units) of cultures. Solutions were incubated at 25-350 C with daily immersion.

| Organism | Growth Medium |
|---|---|
| *Pseudomanas* | Trypticase soy broth |
| *Listeria monocytogenes* | Tryppticase soy broth (Plus) |
| Lactic acid bacteria | MRS broth |
| Yeast (*Candida albicans*) | Saboraud dextrose broth |
| *E. coli* (0157-H7) | Fraser broth | growth medium by bioMerieux (prepackaged, 16×125 mm) sc. Good quality glass tube for optical density (0.0) measurement Sample Analyses Samples of the control and inoculated portions were analyzed initially (Day 0) and

| Test | Medium | Incubationl Time 1 Temperature 1 Atmosphere |
|---|---|---|
| *Listeria monocystogenes* | Trypticase soy agar with yeast | 2-Days/30° C./aerobic |
| Lactic acid Bateria | Deman, Rogasa, Sharpe (MRS/agar) | 5-Days/25° C./ aerobic(plus) |
| *Psedomonas aeruginosa* | Trypticase soy agar | 2-Days/30° C./aerobic |
| Yeast (*Candida albicans*) | Saboraud dextrose | 3-Days/30° C./aerobic |
| *E. coli* (0157-H7) | Fraser broth | 2-Days/35° C./aerobic |

Results and Discussion

A preservative is considered effective if it inhibits the growth of spoilage and/or pathogenic organisms in the specific test matrix. A challenge study was conducted in the two preservatives ESP-1 and OP-1 were added to growth media and the solutions, challenged with pseudomonas, *Listeria monocytogenes*, yeast, lactic acid bacteria and *Escherichia coli* (0157-H7).

Results are show in Tables 2-5. As the dates show, *E. coli* (0157-H7), yeast, did not increase in test samples with either 0.125, 0.250, 0.5 and 1.0% ESP-1 and OP-1 or stored at 30-35° C. for 5 days. By contrast inoculated control samples without test product showed a 6-8 log increase in cells. Data also show lactic acid bacteria, *Pseudomonas* and *Listeria monocytogenes* did not increase in test samples with either 0.25, 0.5, 1.0% ESP-1 and OP-1 stored at 25-30° C. for 2-5 days. By contrast, inoculated control samples without test product showed 6-8 log increase in cells.

Therefore, the test products ESP-1 and OP-1 at concentrations of 0.125, 0.250, 0.50, 1.0% were efficacious in the inhibition of spoilage and pathogenic organisms in laboratory growth media.

Finally, the ESP-1 (eggshell powder) product exhibited improved results over the OP-1 (oyster shell powder) product, *Listeria, Pseudomonas*, lactic acid bacteria, yeast at 0.05-0.125% level.

TABLE 2

EFFICACY OF PRESERVATIVES CHALLENGED WITH *LISTERA* MONOCYTOGENES

| Interval | Replicates | Positive Control (cfu/ml) | ESP-1 (1%) (cfu/ml) | OP-1 (1%) (cfu/ml) | ESP-1 (0.5%) (cfu/ml) | OP-1 (0.5%) (cfu/ml) | ESP-1 (0.25%) (cfu/ml) | OP-1 (0.25%) (cfu/ml) |
|---|---|---|---|---|---|---|---|---|
| Inoculum Level | | 100 | 100 | 100 | 100 | 100 | 100 | 100 |
| Day 0 | 1 | 100 | 0 | 0 | 0 | 0 | <10 | <10 |
| | 2 | 95 | 0 | 0 | 0 | 0 | <10 | <10 |
| | 3 | 96 | 0 | 0 | 0 | 0 | <10 | <10 |
| Day 5 | 1 | 350,000,000 | <10 | <10 | <10 | <10 | <10 | <100 |
| | 2 | 525,000,000 | <10 | <10 | <10 | <10 | <10 | <100 |
| | 3 | 425,000,000 | <10 | <10 | <10 | <10 | <10 | <100 |

| Interval | Replicates | Positive Control (cfu/ml) | ESP-1 (0.125%) (cfu/ml) | OP-1 (0.125%) (cfu/ml) | ESP-1 (0.05%) (cfu/ml) | OP-1 (0.05%) (cfu/ml) |
|---|---|---|---|---|---|---|
| Inoculum Level | | 100 | 100 | 100 | 100 | 100 |
| Day 0 | 1 | 100 | 59 | 100 | 63 | 100 |
| | 2 | 95 | 63 | 93 | 71 | 100 |
| | 3 | 96 | 68 | 96 | 73 | 99 |
| Day 5 | 1 | 350,000,000 | <100 | <50,000 | <100,000 | 175,000,000 |
| | 2 | 525,000,000 | <100 | <50,000 | <100,000 | 225,000,000 |
| | 3 | 425,000,000 | <100 | <50,000 | <100,000 | 315,000,000 |

TABLE 3

EFFICACY OF PRESERVATIVES CHALLENGED WITH LACTIC ACID

| Interval | Replicates | Positive Control (cfu/ml) | ESP-1 (0.125%) (cfu/ml) | OP-1 (0.125%) (cfu/ml) | ESP-1 (0.5%) (cfu/ml) | OP-1 (0.5%) (cfu/ml) | ESP-1 (1%) (cfu/ml) | OP-1 (0.25%) (cfu/ml) |
|---|---|---|---|---|---|---|---|---|
| Inoculum level | | 1500 | 1500 | 1500 | 1500 | 1500 | 1500 | 1500 |
| Day 0 | 1 | 650 | <10 | <10 | <10 | <10 | <10 | <10 |
| | 2 | 610 | <10 | <10 | <10 | <10 | <10 | <10 |
| | 3 | 570 | <10 | <10 | <10 | <10 | <10 | <10 |
| Day 5 | 1 | 675,000,000 | <10 | <10 | <10 | <10 | <10 | <10 |
| | 2 | 925,000,000 | <10 | <10 | <10 | <10 | <10 | <10 |
| | 3 | 750,000,000 | <10 | <10 | <10 | <10 | <10 | <10 |

| Interval | Replicates | Positive Control (cfu/ml) | ESP-1 (0.125%) (cfu/ml) | OP-1 (0.125%) (cfu/ml) | ESP-I (0.5%) (cfu/ml) | OP-1 (0.05%) (cfu/ml) |
|---|---|---|---|---|---|---|
| Inoculum Level | | 1500 | 1500 | 1500 | 1500 | 1500 |
| Day 0 | 1 | 650 | 10 | 100 | 100 | 1000 |
| | 2 | 610 | 10 | 100 | 100 | 1000 |
| | 3 | 570 | 10 | 100 | 100 | 1000 |
| Day 5 | 1 | 675,000,000 | <100 | <100,000 | <1,00,000 | 2,100,000 |
| | 2 | 925,000,000 | <100 | <100,000 | <1,00,000 | <3,150,000 |
| | 3 | 750,000,000 | <100 | <100,000 | <90,000 | 2,650,000 |

TABLE 4

EFFICACY OF PRESERVATIVES CHALLENGED WITH *PSEUDOMONAS*

| Interval | Replicates | Positive Control (cfu/ml) | ESP-1 (1%) (cfu/ml) | OP-1 (1%) (cfu/ml) | ESP-1 (0.5%) (cfu/ml) | OP-1 (0.5%) (cfu/ml) | ESP-1 (0.25%) (cfu/ml) | OP-1 (0.25%) (cfu/ml) |
|---|---|---|---|---|---|---|---|---|
| Inoculum Level | | 50 | 50 | 50 | 50 | 50 | 50 | 50 |
| 1 Day 0 | 1 | 45 | 0 | 0 | 0 | 0 | 0 | 0 |
| | 2 | 39 | 0 | 0 | 0 | 0 | 0 | 0 |
| | 3 | 42 | 0 | 0 | 0 | 0 | 0 | 0 |
| Day 5 | 1 | 680,000,000 | 0 | 0 | <10 | <10 | <10 | <10 |
| | 2 | 650,000,000 | 0 | 0 | <10 | <10 | <10 | <10 |
| | 3 | 790,000,000 | 0 | 0 | <10 | <10 | <10 | <10 |

TABLE 4-continued

EFFICACY OF PRESERVATIVES CHALLENGED WITH *PSEUDOMONAS*

| Interval | Replicates | Positive Control (cfu/ml) | ESP-I (0.125%) (cfu/ml) | OP-I (0.125%) (cfu/ml) | ESP-I (0.05%) (cfu/ml) | OP-I (0.05%) (cfu/ml) |
|---|---|---|---|---|---|---|
| Inoculum Level | | 50 | 50 | 50 | 50 | 50 |
| 1 Day 0 | 1 | 45 | 0 | 0 | 0 | <10 |
| | 2 | 39 | 0 | 0 | 0 | <10 |
| | 3 | 42 | 0 | 0 | 0 | 15 |
| Day 5 | 1 | 680,000,000 | 29 | <100 | <100 | <100,000 |
| | 2 | 650,000,000 | 20 | <100 | <100 | <100,000 |
| | 3 | 790,000,000 | 26 | <100 | <100 | <100,000 |

TABLE 5

EFFICACY OF PRESERVATIVES CHALLENGED WITH YEAST

| Interval | Replicates | Positive Control (cfu/ml) | ESP-1 (1%) (cfu/ml) | OP-1 (1%) (cfu/ml) | ESP-1 (0.5%) (cfu/ml) | OP-1 (0.5%) (cfu/ml) | ESP-1 (0.25%) (cfu/ml) | OP-1 (0.25%) (cfu/ml) |
|---|---|---|---|---|---|---|---|---|
| Inoculum Level | | 200 | 200 | 200 | 200 | 200 | 200 | 200 |
| Day 0 | 1 | 159 | 15 | 18 | 21 | 29 | 21 | 31 |
| | 2 | 100 | 13 | 29 | 19 | 20 | 23 | 29 |
| | 3 | 118 | 19 | 21 | 31 | 16 | 17 | 40 |
| Day 5 | 1 | 8,000,000 | <10 | <10 | <10 | <10 | <10 | <10 |
| | 2 | 12,000,000 | <10 | <10 | <10 | <10 | <10 | <10 |
| | 3 | 9,500,000 | <10 | <10 | <10 | <10 | <10 | <10 |

| Interval | Replicates | Positive Control (cfu/ml) | ESP-1 (0.125%) (cfu/ml) | OP-1 (0.125%) (cfu/ml) | ESP-I (0.05%) (cfu/ml) | OP-1 (0.05%) (cfu/ml) |
|---|---|---|---|---|---|---|
| Inoculum Level | | 200 | 200 | 200 | 200 | 200 |
| Day 0 | 1 | 159 | 35 | 37 | 39 | 29 |
| | 2 | 100 | 26 | 41 | 18 | 45 |
| | 3 | 118 | 21 | 31 | 27 | 51 |
| Day 5 | 1 | 8,000,000 | <10 | <100 | <1,000 | <200,000 |
| | 2 | 12,000,000 | <10 | <100 | <1,000 | <250,000 |
| | 3 | 9,500,000 | <10 | <100 | <1,000 | <150,000 |

TABLE 6

EFFICACY OF PRESERVATIVES CHALLENGED WITH *ESCHERICHIA COLI* (O157-H7)

| Interval | Replicates | Positive Control (cfu/ml) | ESP (1%) (cfu/ml) | OP-1 (1%) (cfu/ml) | ESP-1 (0.5%) (cfu/ml) | OP-1 (0.5%) (cfu/ml) | ESP-1 (0.25%) (cfu/ml) | OP-1 (0.25%) (cfu/ml) |
|---|---|---|---|---|---|---|---|---|
| Inoculun Level | | 100 | 100 | 100 | 100 | 100 | 100 | 100 |
| Day 0 | 1 | 79 | <10 | <10 | <10 | <10 | 0 | <10 |
| | 2 | 81 | <10 | <10 | <10 | <10 | 0 | <10 |
| | 3 | 63 | <10 | <10 | <10 | <10 | <10 | <10 |
| Day 5 | 1 | 325,000,000 | <10 | <10 | <10 | <10 | <10 | <10 |
| | 2 | 496,000,000 | <10 | <10 | <10 | <10 | <5 | <10 |
| | 3 | 298,000,000 | <10 | <10 | <10 | <10 | <5 | <10 |

TABLE 5

| Interval | Replicates | Positive Control (cfu/ml) | ESP-I (0.125%) (cfu/ml) | OP-I (0.125%) (cfu/ml) | ESP-I (0.05%) (cfu/ml) | OP-I (0.05%) (cfu/ml) |
|---|---|---|---|---|---|---|
| Inoculum Level | | 100 | 100 | 100 | 100 | 100 |
| Day 0 | 1 | 79 | <10 | <10 | 49 | 67 |
| | 2 | 81 | <10 | <10 | 51 | 69 |
| | 3 | 63 | <10 | <10 | 59 | 80 |

TABLE 5-continued

| Interval | Replicates | Positive Control (cfu/ml) | ESP-I (0.125%) (cfu/ml) | OP-I (0.125%) (cfu/ml) | ESP-I (0.05%) (cfu/ml) | OP-I (0.05%) (cfu/ml) |
|---|---|---|---|---|---|---|
| Day 5 | 1 | 325,000,000 | <10 | <10 | <100,000 | <150,000 |
|  | 2 | 496,000,000 | <10 | <10 | <100,000 | <150,000 |
|  | 3 | 298,000,000 | <10 | <10 | <100,000 | <150,000 |

CFU = colony forming units per liter

While the invention has been described with reference to specific embodiments, it will be apparent that numerous variations, modifications and alternative embodiments of the invention are possible, and accordingly all such variations, modifications and alternative embodiments are to be regarded as being within the spirit and scope of the present invention as claimed.

What is claimed is:

1. A method of producing a zinc oxide antibacterial agent from eggshells comprising the steps of
   reducing the size of raw eggshells to a particle size sufficient for the intended use of the eggshell;
   removing any excessive liquid from the sized eggshell particles;
   heating the sized eggshell particles in a heating zone at a calcining temperature of about 350° C. to about 400° C. for an effective amount of time to produce zinc oxide and removing the calcined eggshells containing zinc oxide from the heat;
   cooling the heated eggshell particles;
   drying the eggshell particles; and
   reducing the size of the heated, dried eggshell particles a second time to produce a calcined eggshell powder with antibacterial properties containing zinc oxide.

2. The method according to claim 1, wherein the size of the raw eggshell particle is reduced to about ¼ inch by grinding.

3. The method according to claim 1, wherein the eggshell particles are heated to remove organic matter from the calcined eggshell particles.

4. The method according to claim 1 wherein the calcined eggshell particles are ground to a particle size of about 150 microns to form a powder.

5. The method according to claim 1 wherein the calcined eggshell particles are ground to a particle size of about 1 to 50 microns.

6. The method according to claim 1 wherein the eggshell powder is free of pathogens.

7. The method according to claim 1, wherein the size of the raw eggshell particle is reduced to about ¼ inch diameter.

* * * * *

UNITED STATES PATENT AND TRADEMARK OFFICE
CERTIFICATE OF CORRECTION

PATENT NO.        : 8,859,010 B2
APPLICATION NO.   : 10/535779
DATED             : October 14, 2014
INVENTOR(S)       : Fred K. Suzuki et al.

It is certified that error appears in the above-identified patent and that said Letters Patent is hereby corrected as shown below:

In the drawing on the Title Page under the (abstract), please replace "MnO" with --MgO--.

In the Drawings

Sheet 1, Figure 1, please replace "MnO" with --MgO--.

Signed and Sealed this
Seventeenth Day of February, 2015

Michelle K. Lee
*Deputy Director of the United States Patent and Trademark Office*